United States Patent [19]
Han et al.

[11] Patent Number: 6,066,748
[45] Date of Patent: May 23, 2000

[54] PROCESS OF EXTRACTING TAXOL® FROM TAXUS CUSPIDATA

[76] Inventors: Man Woo Han, Lotte Apt. No. 1103, 109-Dong 220-2 Nai-Dong, Suh-Ku; Jae Kuk Yoo, Kyunsung Kunmaul Apt. No 303, 117-Dong, Kalma-Dong, Suh-ku, both of Taejeon City; Nam Doo Hong, 200-205 Sungsan-Dong, Mapo-Ku, Seoul, all of Rep. of Korea

[21] Appl. No.: 09/068,318

[22] PCT Filed: Jan. 19, 1998

[86] PCT No.: PCT/IB98/00079

§ 371 Date: May 8, 1998

§ 102(e) Date: May 8, 1998

[87] PCT Pub. No.: WO99/37796

PCT Pub. Date: Jul. 29, 1999

[51] Int. Cl.$^7$ .................................................. C07D 305/14
[52] U.S. Cl. ........................................... 549/510; 549/511
[58] Field of Search ....................................... 549/510, 511

[56] References Cited

U.S. PATENT DOCUMENTS

| 5,723,635 | 3/1998 | Durand et al. | 549/510 |
| 5,736,366 | 4/1998 | Margraff | 549/510 |
| 5,744,333 | 4/1998 | Cociancich et al. | 549/510 |

*Primary Examiner*—Ba K. Trinh
*Attorney, Agent, or Firm*—Bachman & LaPointe, P.C.

[57] ABSTRACT

The present invention teaches a method of extracting TAXOL® from the leaves of taxus cupidata plants. The process comprises a series of steps, including the concentration of the extracts obtained from the plant, the separation of the aqueous and chloroform phases, and several purification procedures. In addition, the present invention teaches a multi-step process wherein the virtual removal of chlorophyll is achieved prior to the introduction of the extract into the silica gel packing material. This prevents the deactivation of the silica gel packing material by chlorophyll in the extract solution.

19 Claims, 3 Drawing Sheets

PROCESS OF EXTRACTING TAXOL® FROM TAXUS CUSPIDATA

BACKGROUND OF THE INVENTION

1. Field of the Invention

The present invention relates generally to medicines and pharmaceutical products derived from plants, and specifically to a process of extracting TAXOL® from the leaves of taxus cuspidata plants.

2. Description of the Prior Art

TAXOL® (paclitaxel) is one of a class of drugs called taxanes. These types of drugs promote polymerization of tubulin and stabilize the structure of intracellular microtubules. This process has the effect of inhibiting the normal dynamic reorganization of the microtubules that is necessary for interphase and mitotic functions. Paclitaxel may also potentiate the cytotoxic effects of radiation.

The pharmacokinetics of paclitaxel vary considerably depending on the dosage and duration of infusion. Plasma concentrations of paclitaxel decline in a biphasic manner following injection. Increasing a 24-hour infusion from 135 mg/mL to 175 mg/mL increased Cmax by 87% while the area under the plasma concentration-time curve (AUC) remained constant. Increasing a 3-hour infusion increased Cmax by 68% and the AUC by 89%. With the 24-hour infusion of paclitaxel, the mean apparent volume of distribution in the steady state ranged from 227 to 688 L/m2, indicating extensive extravascular distribution or tissue binding. In vitro studies show that 89% to 98% of paclitaxel is bound to human serum proteins. Paclitaxel may undergo hepatic metabolism in humans. Studies have demonstrated extensive nonrenal clearance. The disposition of paclitaxel in patients with renal or hepatic dysfunction has not yet been determined.

In two studies of ovarian cancer patients receiving paclitaxel in doses of 135 mg/mL or 175 mg/mL, the response rates were 22% and 30%, respectively, with 6 complete and 18 partial responses among 92 patients. Duration of response was 7.2 and 7.5 months, respectively, with median survival rates of 8.1 months and 15.9 months. A Phase III study of 471 breast cancer patients receiving paclitaxel in doses of 135 mg/mL or 175 mg/mL infused over 3 hours indicated an overall response rate of 26%, with 17 complete and 99 partial responses. The median duration of response was 3.5 months, and the median survival time was 11.7 months.

TAXOL® should not be used for patients with hypersensitivity to polyoxyethylated castor oil (Cremaphor EL) or TAXOL®. Patients should be pretreated with corticosroids (e.g., dexamethasone and diphenhydramine) and H2-receptor antagonists (cimetidine or ranitidine.) Patients receiving concomitant ketaconazole should be treated with caution. Two percent of patients receiving Taxol have severe hypersensitivity reactions that are characterized by dyspnea, hypotension, angioedema, and generalized urticaria. One incident of progressive hypotension, possibly related to the use of TAXOL®, resulted in the death of the patient. Other side effects include bone marrow suppression, abnormal ECG, peripheral neuropathy, myalgia and arthralgia, alopecia, injection site reaction, nausea, vomiting, diarrhea, and mucositis. Continuing safety surveillance has produced rare reports of hepatic necrosis, hepatic encephalopathy, phlebitis, and cellulitis. Available as a clear, colorless to slightly yellow, viscous solution, TAXOL® is packaged in single-dose vials containing 30 mg/5 mL. After dilution with a suitable parenteral fluid to 0.3 to 1.2 mg/mL, 135 mg/m2 paclitaxel is infused intravenously over 24 hours every 3 weeks for ovarian cancer. The dose level for breast cancer is 175 mg/mL, administered in the same manner. TAXOL® treatment should not be repeated until neutrophil and platelet counts return to 1500 cells/mm2 and 100,000 cells/mm2, respectively.

The National Cancer Institute performed research on TAXOL® in the 1960's, examining some 35,000 botanical species in search for plants that could yield cancer-inhibiting products. The cancer-inhibiting material extracted from the bark of Taxus Brevifolia was reported to have beneficial effects upon patients suffering from leukemia, lung cancer, and other types of cancer. According to statistics issued by the National Cancer Institute, TAXOL® is reported to have cured 30% of the patients suffering from ovarian cancer who received dosages of TAXOL®. Likewise, 50% of patients suffering from breast cancer and 20% of patients suffering from lung cancer also were cured by the application of TAXOL®. Schiff additionally reported the effectiveness of TAXOL® in impeding the growth of cancers. (Schiff, P. B., J. Fant and S. B. Horwitz, Nature, 277, 665 (1979)) In addition, the analytical analysis of TAXOL® was accomplished in 1971. (E. K. Rowinsky et al., J. National Can. Inst., 82, 11247 (1990))

In December of 1992, the Food and Drug Administration (FDA) approved the natural form of paclitaxel for treatment of metastatic ovarian cancer after failure of first-line or subsequent chemotherapy, and the use of paclitaxel for the treatment of metastatic breast cancer received marketing approval in April of 1994.

TAXOL® is a complex compound containing unsaturated carbons. Although researchers reported total synthesis of TAXOL® in 1994, the process was so expensive that it was deemed that it was not commercially feasible to produce this form of TAXOL® on a production level. Therefore, TAXOL® can only be obtained currently through natural sources, namely yew trees.

Accordingly, the demand for TAXOL® is ever increasing. The supply of TAXOL®, however, is not sufficient to provide for the needs of all the patients who are currently suffering from cancer. TAXOL® is so scarce that adequate amounts cannot be provided for the research of testing its effectiveness against skin cancer and other types of lung cancer.

Presently, TAXOL® is primarily obtained from the bark of yew trees. This bark contains about 0.02% TAXOL by weight. Because the bark must be removed from the tree in order to effectively extract the TAXOL®, the tree subsequently dies after the removal of its bark. This restricts the amount of TAXOL® which can be extracted from each tree, and also severely limits the total amount of TAXOL® which may be extracted, since new trees must be planted and matured before they can be stripped of their bark. The fact that yew trees grow very slowly further hinders attempts to produce TAXOL®. From an environmental standpoint, the constant uprooting of yew trees may have severe effects on the natural habitats that accommodate the trees.

Methods of extracting TAXOL® from yew tree leaves were reported in Korean Patent Nos. 95-10903, 95-25034 and 97-1339. These-patents pertain to techniques used to analyze the TAXOL® content in yew tree leaves. They do not disclose commercially feasible methods of the extraction of TAXOL from yew tree leaves. The primary element which determines the economic feasibility of the production of TAXOL® is the removal of chlorophyll from the yew tree leaves. Chlorophyll deactivates silica gel packing material, which is used in purification columns and is necessary for the purification of the extracts from the yew tree leaves.

The present invention provides a method that not only discloses the effective removal of chlorophyll from yew tree leaves, but also the extraction of substantially pure TAXOL® from the leaves. Specifically, the present invention discloses a process which yields 80–100 mg of at least 98% pure TAXOL® from 1 kg of yew tree leaves.

SUMMARY OF THE INVENTION

The present invention teaches a method of extracting TAXOL® from the leaves of taxus cuspidata plants. The chlorophyll inherently existing in the leaves of taxus cuspidata has caused problems in the extraction processes. Specifically, the presence of chlorophyll in the extract solution complicates silica gel column chromatography, which is used in the extraction process. The present invention, however, teaches a multi-step process wherein the virtual removal of chlorophyll is achieved prior to the introduction of the extract into the silica gel packing material. This process includes but is not limited to the following steps: 1) concentration of the extracts from taxus cuspidata leaves using a solvent, including but not limited to methanol; 2) separation of chloroform soluble elements by distribution of the concentrated extract solution into a polar water phase and a non-polar chloroform phase; 3) further separation of the chloroform phase concentrate using a separation means, including but not limited to a strong anion ion exchange resin; 4) purification of the pregnant solution obtained from the previous step 3 using a separation means, including but not limited to ordinary column chromatography; 5) further purification of the pregnant solution obtained from the previous step 4 using a separation means, including but not limited to reverse column chromatography; 6) further purification of the pregnant solution obtained from the previous step 5 using a separation means, including but not limited to semi-prep HPLC. This process is an effective and economically feasible method of extracting TAXOL® from the leaves of taxus cuspidata. This process may also be utilized to extract TAXOL® from other TAXOL® bearing plants.

BRIEF DESCRIPTION OF THE DRAWINGS

For a better understanding of the principle and nature of the present invention, reference should be made to the following detailed description taken in connection with the accompanying drawings in which.

DETAILED DESCRIPTION OF THE PREFERRED EMBODIMENT

Figure 1:
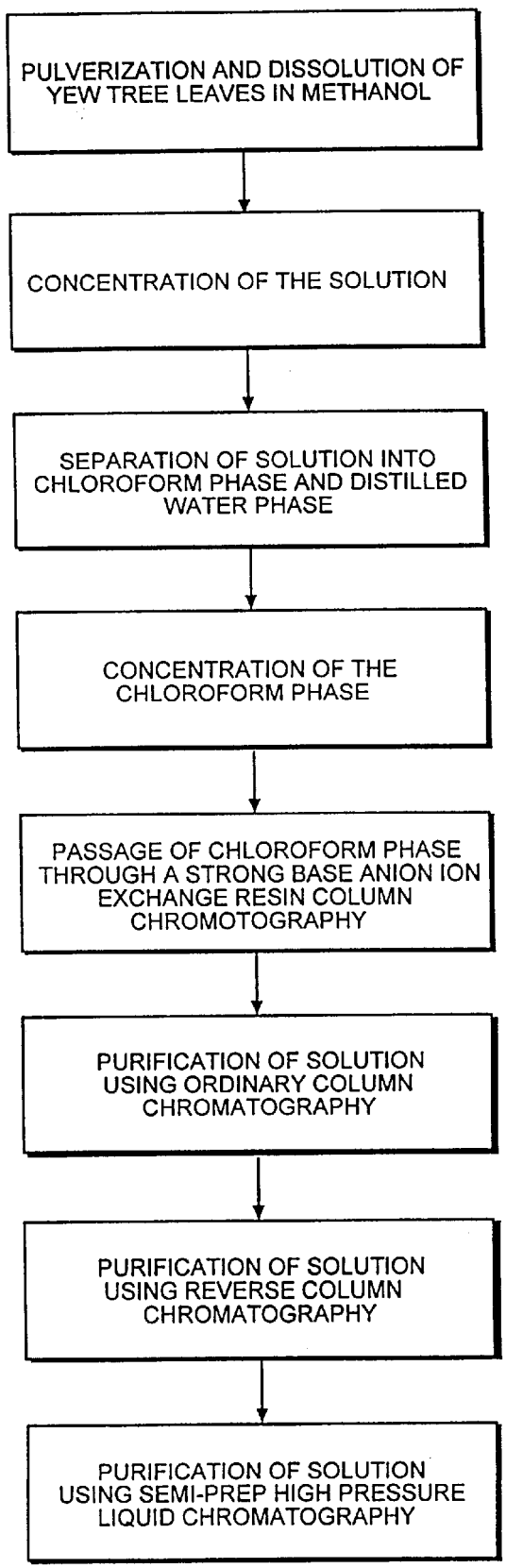
FIG. 1 is a block flow diagram of the process taught by the present invention.
Figure 2A:
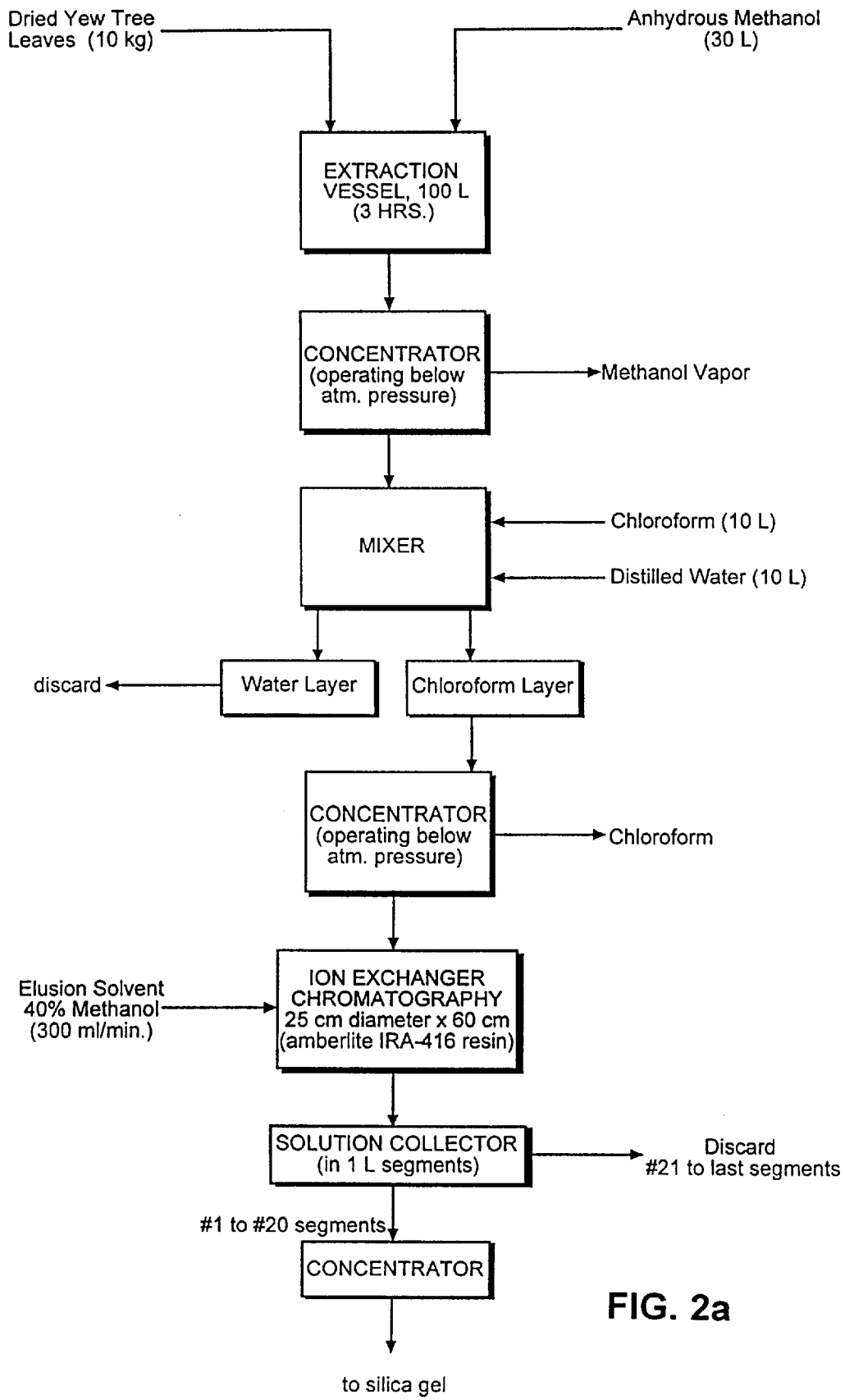
FIG. 2a is a block flow diagram of the first example of the process taught by the present invention.
Figure 2B:
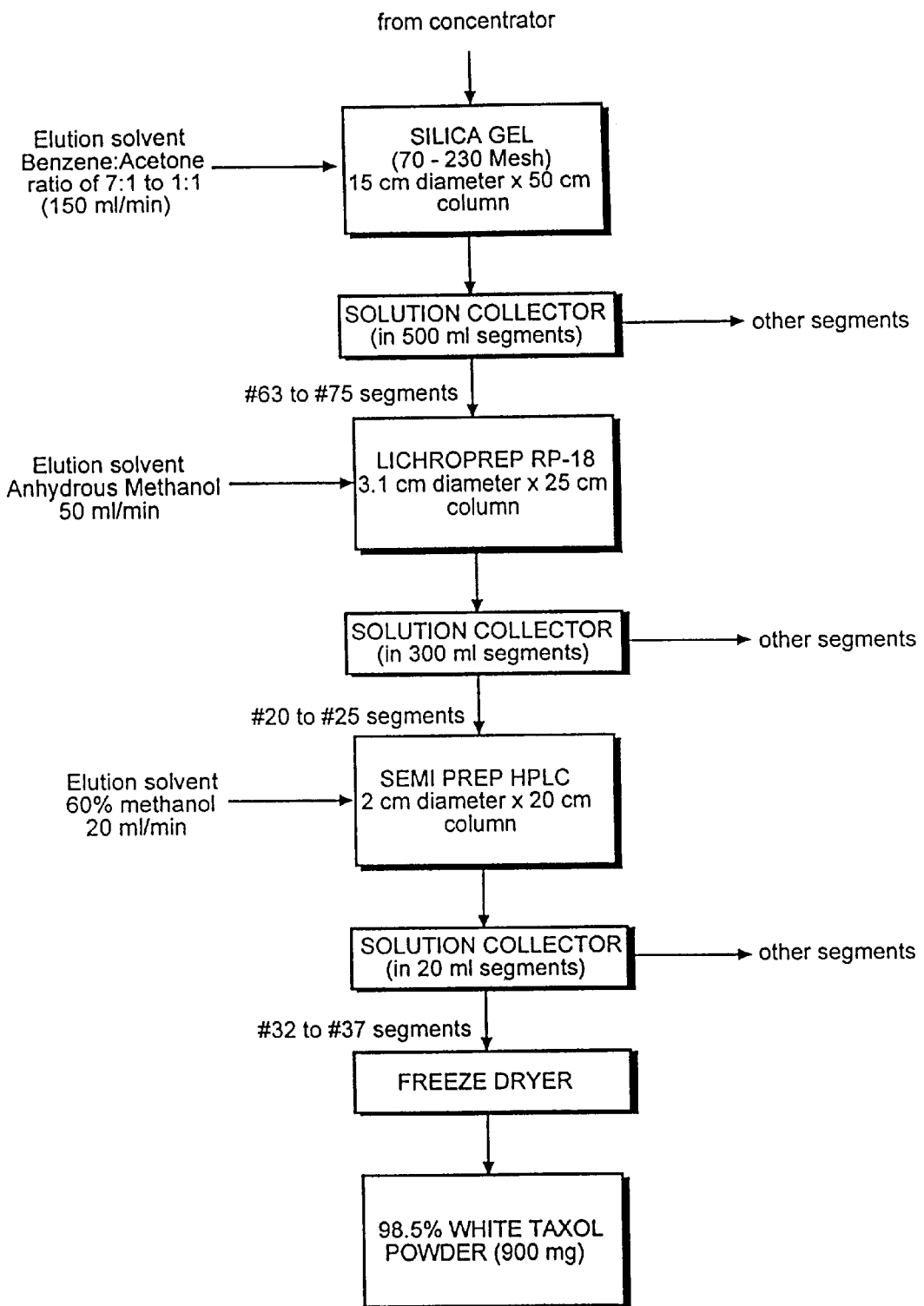
FIG. 2b is a continuation of the block flow diagram of the first example of the process taught by the present invention.

The present invention teaches a method of extracting TAXOL from the leaves of taxus cuspidata plants, comprising a multi-step process utilizing several separation and purification techniques The process teaches the unprecedented method of extracting TAXOL which is economically viable. The following are three examples of the process which is taught by the present invention:

EXAMPLE 1:

10 kg of dried yew tree leaves obtained from Jae Ju Island, South Korea were crushed. The crushed leaves were placed in an 100 liter extraction vessel, wherein 30 liters of anhydrous methanol was added. The solution was agitated for 3 hours at room temperature, and the TAXOL containing material was extracted. This process was repeated twice.

The methanol extract was condensed in a 20-liter vessel, operating below atmospheric pressure. 10 liters of chloroform was added, followed by 10 liters of distilled water. The resulting solution was vigorously agitated, and allowed to settle, and two phases were obtained. The polar water layer was removed, along with the impurities in it.

The chloroform layer was concentrated in a concentrator vessel operating below atmospheric pressure. The concentrate was then passed through an Amberlite IRA-416 ion exchange resin column with dimensions of 25 cm diameter × 60 cm, and made of glass. 40% (by volume) methanol at a flow rate of 300 ml/min was used as an elusion solvent.

The eluted solution was separately collected at 1 liter segments. Fraction numbers 1 through 20 were selected, and the remaining fractions were discarded to remove the chlorophyll in solution. The useful segments were concentrated, and passed through a silica gel column, with Silica Gel 60 (70–230 Mesh, Merck Co.). The elution solvent used was a benzene acetone mixture at a variable volume ratio of 7:1 to 1:1, respectively, at a flow rate of 150 ml/min, through the glass column. This was the first stage separation/purification process. The eluted solution was collected at 500 ml segments to select only pregnant segment numbers 63 to 75.

The pregnant segment was concentrated, and passed through Lichroprep RP-18 (40–63 µm, Merck Co.) glass column with dimensions of 3.1 cm diameter × 25 cm. The elution solution that was used was anhydrous methanol at a flow rate of 50 ml/min. This was the second stage separation/purification. The eluted solution was collected in 300-ml segments to select only fraction numbers 20–25 as the pregnant fraction.

The pregnant fraction was concentrated and passed through Semi-prep HPLC (SCL-8A HPLC of Shimadzu, Japan and DC-1200 Fraction Collector of Eyela, Japan), which is the last stage separation/purification step. The column which was used was a pre-packed ODS (Octadecyl silane) column (SG120 column, Shiseido Corp., Japan), with dimensions of 2 cm diameter × 20 cm.

The elution solvent was 60% (by volume) methanol at a flow rate of 20 ml/min. The eluted solution was collected in 20 ml segments to select segment numbers 32 to 37 as the pregnant segments. The latter was freeze dried to obtain 900 mg of white TAXOL powder of 98.5% purity.

EXAMPLE 2

The process delineated in EXAMPLE 1 was repeated, with the following exceptions:

1) 50% (by volume) methanol was used;
2) the useful fraction, after the removal of the chlorophyll-containing fraction, was concentrated and passed through the glass column using an n-Hexane/ethyl acetylene mixture at a variable volume ratio between 5:1 and 1:1, respectively;
3) 55% (by volume) methanol was used as the elution solvent.

The pregnant segment was concentrated to double its original molarity and was crystallized at 0 degrees C to obtain an 880 mg yield of white TAXOL powder of 99.1% purity.

EXAMPLE 3

The process delineated in EXAMPLE 1 was repeated, with the following exceptions:

1) 60% (by volume) methanol was used as the elution solvent after the separation of the chloroform phase at below atmospheric pressure;

2) the useful segment after removal of the chlorophyll containing segments was eluted with the elution solvent consisting of n-Hexane/ethyl acetylene mixture at variable volume ratios between 3:1 and 1:1.

The pregnant solution was concentrated and passed through Semi-prep HPLC to yield 960 mg of white TAXOL powder of 98.7% purity.

We claim:

1. A process of extracting TAXOL from yew tree leaves, where said process comprises:
   a) concentration of extract from said yew tree leaves using methanol as a solvent;
   b) distribution of said extract from said yew tree leaves into a two phase system, said two phases comprising a water phase and a chloroform phase;
   c) separation of said two phase system using a strong anion ion exchange resin as a separation means;
   d) purification of the pregnant solution obtained from said chloroform phase from said previous separation, using ordinary column chromatography as a purification means;
   e) further purification of said pregnant solution obtained from said purification, using reverse column chromatography as a purification means;
   f) further purification of said pregnant solution obtained from said purification, using semi-prep high pressure liquid chromatography as a purification means.

2. A process of extracting TAXOL from yew tree leaves as mentioned in claim 1, wherein said solvent used for said concentration of said extract is anhydrous methanol.

3. A process of extracting TAXOL from yew tree leaves as mentioned in claim 1, wherein said strong anion ion exchange resin is Amberlite IRA-416 (Rohm and Haas, U.S.A.).

4. A process of extracting TAXOL from yew tree leaves as mentioned in claim 1, wherein said strong anion ion exchange resin is Permutit ESB (Permutit AG, Germany).

5. A process of extracting TAXOL from yew tree leaves as mentioned in claim 1, wherein said strong anion ion exchange resin is Dowex 2-×8 (Dow Chemical Co., U.S.A.).

6. A process of extracting TAXOL from yew tree leaves as mentioned in claim 1, wherein elution solvent used in said separation of said two phase system is in the range between 40% and 60% by volume methanol.

7. A process of extracting TAXOL from yew tree leaves as mentioned in claim 1, wherein packing material used in said purification of said pregnant solution is silica gel.

8. A process of extracting TAXOL from yew tree leaves as mentioned in claim 7, wherein said silica gel is silica gel 60 (63–200 μm).

9. A process of extracting TAXOL from yew tree leaves as mentioned in claim 7, wherein said silica gel is silica gel 40 (63–200 μm).

10. A process extracting TAXOL from yew tree leaves as mentioned in claim 7, wherein said silica gel is silica gel 60 (200–500 μm).

11. A process of extracting TAXOL from yew tree leaves as mentioned in claim 1, wherein elusion solvent used in purification of said pregnant solution using ordinary column chromatography is a mixture of benzene and acetone between the volume ratio range of 7:1 and 1:1, respectively.

12. A process of extracting TAXOL from yew tree leaves as mentioned in claim 1, wherein elusion solvent used in purification of said pregnant solution using ordinary column chromatography is a mixture of hexane and acetate between the volume ratio range of 5:1 and 1:1, respectively.

13. A process of extracting TAXOL from yew tree leaves as mentioned in claim 1, wherein elusion solvent used in purification of said pregnant solution using ordinary column chromatography is a mixture of hexane and acetone between the volume ratio range of 3:1 and 1:1, respectively.

14. A process of extracting TAXOL from yew tree leaves as mentioned in claim 1, wherein packing material used in purification of said pregnant solution using reverse column chromatography is Lichroprep RP-18 (40–63 μm, Merck Co., U.S.A.).

15. A process of extracting TAXOL from yew tree leaves as mentioned in claim 1, wherein packing material used in purification of said pregnant solution using reverse column chromatography is Lichroprep RP-2 (25–40 μm, Merck Co., U.S.A.).

16. A process of extracting TAXOL from yew tree leaves as mentioned in claim 1, wherein packing material used in purification of said pregnant solution using reverse column chromatography is Lichroprep RP-8 (40–63 μm, Merck Co., U.S.A.).

17. A process of extracting TAXOL from yew tree leaves as mentioned in claim 1, wherein elusion solvent used in purification of said pregnant solution using reverse column chromatography is anhydrous methanol.

18. A process of extracting TAXOL from yew tree leaves as mentioned in claim 1, wherein column used in purification of said pregnant solution using semi-prep high pressure liquid chromatography is an ODS (octadecyl silane) column.

19. A process of extracting TAXOL from yew tree leaves as mentioned in claim 1, wherein elusion solvent used in purification of said pregnant solution using semi-prep high pressure quid chromatography is in the range between 50% and 65% by volume methanol.

* * * * *